United States Patent [19]
Jones et al.

[11] Patent Number: 5,360,738
[45] Date of Patent: Nov. 1, 1994

[54] METHOD OF QUANTITATIVE ANALYSIS OF DRILLING FLUID PRODUCTS

[75] Inventors: Timothy Jones, Cottenham; Trevor Hughes, Cherry Hinton, both of England

[73] Assignee: Schlumberger Technology Corporation, Houston, Tex.

[21] Appl. No.: 73,271

[22] Filed: Apr. 16, 1993

Related U.S. Application Data

[63] Continuation of Ser. No. 601,471, Oct. 22, 1990, abandoned.

[30] Foreign Application Priority Data

Oct. 28, 1989 [GB] United Kingdom .............. 8924346.3
May 23, 1990 [GB] United Kingdom .............. 9011527.0

[51] Int. Cl.$^5$ ............................................. G01N 33/24
[52] U.S. Cl. ......................................... 436/30; 73/153; 250/255; 436/29
[58] Field of Search .................... 73/153; 250/255; 436/29, 30

[56] References Cited

U.S. PATENT DOCUMENTS

| | | | |
|---|---|---|---|
| 3,631,246 | 12/1971 | De Friez | 250/252.1 A |
| 4,321,465 | 3/1982 | Stover et al. | 250/255 |
| 4,433,239 | 2/1984 | Thompson | 250/255 |
| 4,608,859 | 9/1986 | Rockley | 73/153 |
| 4,800,279 | 1/1989 | Hieftje et al. | 250/255 |
| 4,839,516 | 6/1989 | Freeman et al. | 250/255 |
| 4,878,382 | 11/1989 | Jones et al. | 73/153 |
| 4,996,421 | 2/1991 | Rai et al. | 250/255 |
| 5,161,409 | 11/1992 | Hughes et al. | 73/153 |

FOREIGN PATENT DOCUMENTS 316985 5/1989 European Pat. Off. .

OTHER PUBLICATIONS

D. P. Salisbury et al. *Spectroscopy* 1986, 1, 44–47.
R. W. Snyder et al. *Fuel*, 1983, 62, 1205–1214.
K. R. Beebe et al. *Anal. Chem.* 1987, 59, 1007A–1017A.
Mills, Brad "Continuous Determination of Oil and Gas Content of Drilling Mud Helpful" *the Oil Weekly*, 1938, 90, 18–20.
Leyden, D. E. et al., "Diffuse Reflectance Fourier Transform IR Spectroscopy", *Trends in Analytical Chemistry*, 1988, 7, 164–169.
Fuller, M. P., et al., "Infrared Microsampling by Diffuse Reflectance Fourier Transform Spectrometry", *Appl. Spectrosc.*, 1980, 34, 533–539.
Brown, James M. et al., "The Quantitative Analysis of Complex, Multicomponent Mixtures by FT-IR; The Analysis of Minerals and of Interacting Organic Blends", *Chemical, Biological and Industrial Applications of Infrared Spectroscopy*, pp. 111–128, 1985, Great Britain.

*Primary Examiner*—James C. Housel
*Assistant Examiner*—Arlen Soderquist
*Attorney, Agent, or Firm*—Wayne I. Kanak

[57] ABSTRACT

A method of quantitative analysis of products, such as barite, bentonite or polymers, in a drilling fluid circulating in a wellbore being drilled is described. The method includes the steps of sampling the drilling fluid, and analysing the sample to determine the density of the fluid and the weight fraction of solids in the fluid. In addition, a known weight of the sample is dried to constant weight so as to obtain the products under the form of solids, which solids are analysed by an infrared spectroscopy technique. The concentration of the products in the drilling fluid is then determined. The method can be applied to the control of the drilling operation by monitoring the quantity of products added to the drilling fluid, such as barite and polymers, or a product coming from the borehole wall or the underground formation being drilled. The invention also applies to the control of the working condition of the mud solids equipment.

17 Claims, 8 Drawing Sheets

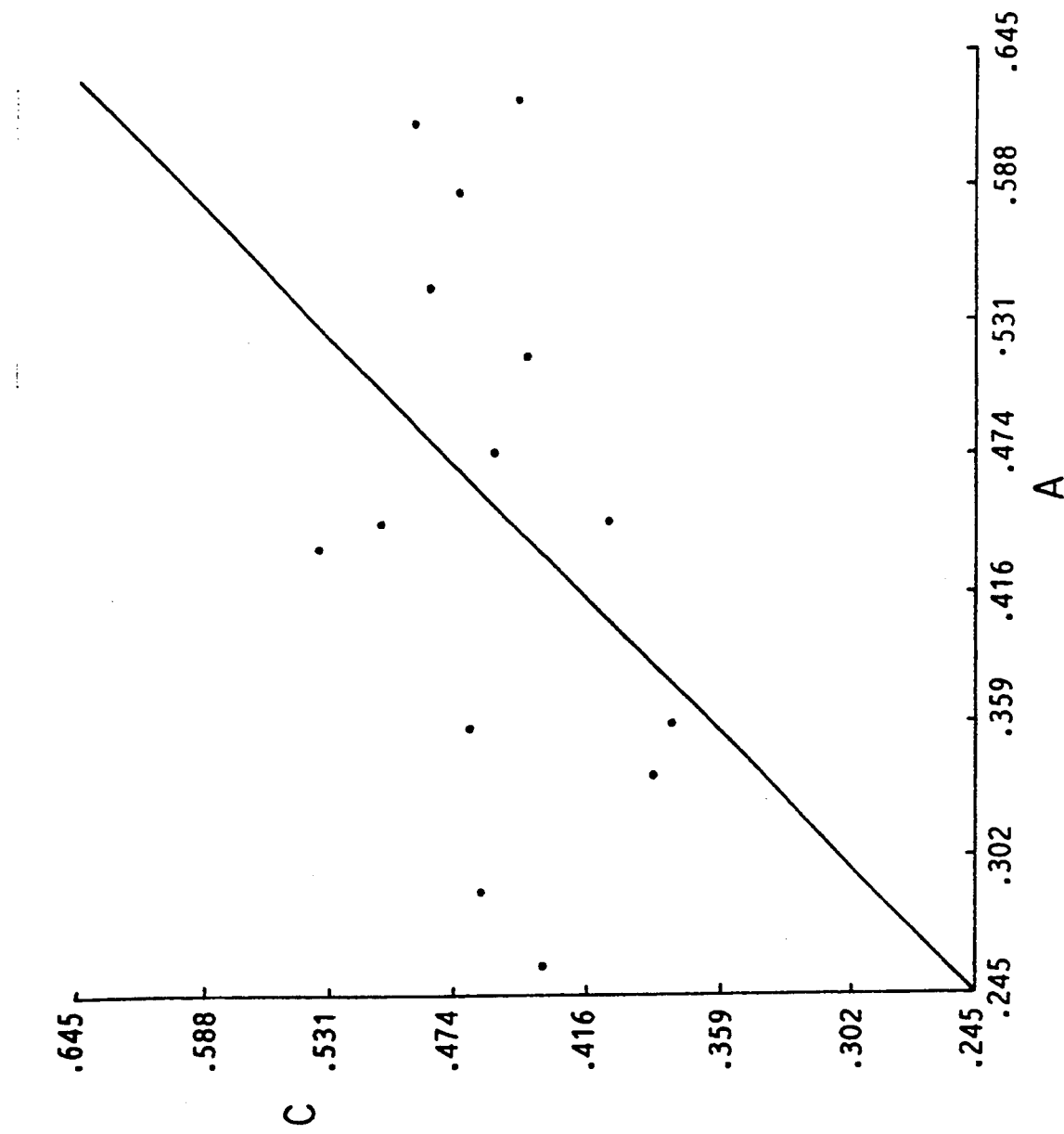

METHOD OF QUANTITATIVE ANALYSIS OF DRILLING FLUID PRODUCTS

This is a continuation of application Ser. No. 07/601,471 filed Oct. 22, 1990, now abandoned.

The present invention relates to a method of quantitative analysis of products in a drilling fluid (usually called "mud") used to drill a well.

In the rotary drilling of wells, such as hydrocarbon wells, a drilling fluid or mud is continuously circulated from the surface down to the bottom of the hole being drilled and back to the surface again. The mud has several functions, one of them being to transport the cuttings drilled by the drill bit up to the surface where they are separated from the mud. Another function is to impose an hydrostatic pressure on the walls of the borehole so as to avoid a collapse of the borehole and an influx of gas or liquid from the formations being drilled. The characteristics of the mud are therefore important to monitor and to keep within certain limits. For example, the density must be large enough so as to exert a certain hydrostatic pressure on the formations but not too large to fracture these formations. The viscosity of the mud is also an important characteristic since it contributes to the cuttings transport capability of the mud. Weighting materials, barite for example, are added to the mud to make it exert as much pressure as needed to contain the formation pressures. Clay, such as bentonite clay, is added to the mud so as to keep the drilled curings in suspension as they move up the hole. The clay also sheathes the wall of the hole. This thin layer of clay, called filter cake, reduces the loss of mud to permeable formations caused by filtration. Numerous chemicals are available to give the mud the exact properties it needs to make it as easy as possible to drill the hole.

Drilling muds are of two main types, distinguished by whether water or oil is used as the continuous phase. Water-base muds are typically suspensions of bentonite clay, to which further heavier minerals (usually barite), polymers and surfactants are added to optimise the rheology and other physical properties for a particular job.

The most common oil-base drilling fluids are water-in-oil emulsions where micron-sized brine droplets, stabilised by emulsifier, are dispersed in a mineral oil, along with organophilic clays, weighting minerals, wetting agents and oil-soluble viscosifiers.

In addition to the products added in the drilling mud for specific purposes, other products coming from the formation being drilled and/or from the borehole wall can be present in the mud. These products are in the form of tiny particles of solids (an average diameter being about 50–100 microns) and are usually called "fines". Examples of "fines" are silica (quartz), carbonates and dispersed clay particles. Hereinafter the term "product" issued to designate both the mud additives and the "fines".

The growing concern over the environmental impact of oil-based drilling fluids has lead to an increasing reliance on water-based muds. An important aspect of water-based muds is the use of water-soluble polymers to control the main functions of the mud: rheology, fluid loss and shale stabilisation. Both naturally-occurring and synthetic polymers have found extensive use in water-based muds, ranging from low molecular weight dispersants to high molecular weight shale stabilising polymers. The commonest naturally-occurring polymers used in drilling fluids are the polysaccharides, which include guar gum, carboxymethyl cellulose, corn starches and xanthan gum. In recent years there has been increased interest in synthetic polymers which generally attempt to extend the temperature and salinity/hardness limits of the naturally-occurring polymers.

Despite the extensive use of polymers in water-based drilling fluids, there are currently no recommended API (American Petroleum Institute) techniques for the determination of the polymer content of such muds. Methods which have been developed to determine polymer concentration invariably use mud flitrate, ie, the polymer contained in the aqueous phase of the mud which is separated from the mud solids. Recent examples have been the measurement of the concentration of lignosulphonate and polyacrylamide polymers by ultraviolet/visible spectrophotometry; however, in seawater-based muds the absorption of the electrolytes interferes with the method for polyacrylamide. Other techniques include derivatisation and polymer degradation on heating. An example of the latter technique is the determination of polyacrylamide concentration by quantitative analysis of the ammonia released on thermal degradation.

Techniques that require separation of a polymer solution from the drilling mud are unsatisfactory, as full recovery of the polymer is not likely. Many of the polymers which are added to the mud, particularly the high molecular weight polymers, are done so with the specific purpose of adsorption on the mud solids. Similarly, during a filtration process, a filter cake is formed which very likely blocks or retains the polymer.

The net result of the normal filtration process, eg, using a high pressure filtration cell, is to produce a polymer solution whose polymer content is unlikely to be representative of the mud as a whole. Other separation processes, such as centrifugation or even cross-flow filtration which results in the continuous removal of the filter cake, are also unsatisfactory as they do not recover polymer adsorbed on the solids.

Bentonite concentration in the drilling mud is usually determined at the rig site by a method based on the adsorption by the bentonire of dyes such as methylene blue. However, the methylene blue interacts with certain polymers, such as carboxymethyl cellulose (CMC), and the method is therefore far from being accurate.

The typical method used to determine the barite content of the mud is from the measurement of mud density. A mass balance analysis tells the mud engineer how much barite remains in the mud, and therefore how much is being ejected by the solids removal equipment (shale shaker, hydrocyclone, mud cleaner, etc) used to clean the mud returning at the surface from the borehole. This method, however, does not account for the low-gravity drilled solids, such as the "fines", and is therefore not satisfactory.

Infrared spectroscopy, and more particularly Fourier transform infrared spectroscopy, has been used to analyse the mineral composition of rock samples, such as shale samples in the article entitled "The quantitative analysis of complex, multicomponent mixtures by FT-IR; the analysis of minerals and of interacting organic blends" by James M Brown and James J Elliott, published in the book "Chemical, Biological and Industrial Applications of Infrared Spectroscopy", a Wiley-Interscience publication, 1985. Another example is the determination of mineral composition of solids (core samples or drilled cuttings) coming from the drilled formation (see U.S. Pat. Nos. 4,608,859 and 4,839,516). These analyses relate to the formation being or having been drilled, and concern only coarse solids (not the mud) which, in the case of the drilled cuttings, are separated from the drilling mud by the solids control equipment.

A method of monitoring the drilling mud is described in EP Patent Application 0,282,231, in which the mud solids (other than the cuttings) are analysed at the rig site by ion chromatography, a technique completely different from the one used in the present invention.

The present invention proposes a method of analysis of the drilling fluid, and more particularly of its contained products.

One object of the invention is to provide a method of determining the concentrations of the main products—or at least one product—present in a drilling fluid.

Another object is to provide a method of determining the variations in the concentrations of the main products of the drilling fluid, compared with the specifications of the drilling fluid. Any variation deemed too large by the driller can then be corrected, for example by adding a known quantity of a product when a deficiency in that product is revealed by the mud analysis.

Another object of the invention is to assess the working conditions of the mud solids equipment at the surface.

A further object of the invention is to monitor the drilling operation by controlling the mud composition—and more particularly by monitoring the presence in the mud of products coming from the borehole wall and/or the formation being drilled. As an example, the concentration of carbonates in the drilling fluid could be monitored since it would indicate that the bit is drilling into a carbonate formation: this is interesting because carbonate fines often lead to unstable rheology of the mud and poor quality of the filter cake formed on the borehole wall.

The technique of analysis of the present invention involves no separation process of the product from the mud, such as filtration, and allows the quantitative analysis of the products, such as polymer(s) present in a drilling fluid. The proposed method has also the advantage of determining the concentration of the solids in the mud by one analysis only: the polymer(s) and the other mud products such as added mud solids (eg, barite, bentonire) and "fines" (eg, carbonates, quartz) can be quantified simultaneously.

More precisely, the invention relates to a method of quantitative analysis of products in a drilling fluid, according to which the fluid is sampled and the sample is analysed, the method comprising the following steps:
  determining the density $d_m$ of the fluid sample,
  drying a known weight of fluid $M_m$ to constant weight so as to obtain the products in the form of dried solids,
  determining the weight fraction of solids $W_s$ in the fluid,
  preparing a known weight of dried solids to form a powder suitable for infrared analysis,
  analysing the powder in a spectrometer to obtain an infrared spectrum, and
  determining a value characteristic of the concentration of at least one of the products in the drilling fluid, from the spectrum, the value of the density $d_m$ of the fluid sample and the value of the weight fraction of the solids $W_s$ in the fluid.

The products are mainly polymer(s), drilled clays, bentonite clay, barite, quartz and carbonates. The spectrum is preferably obtained by Fourier transform infrared (FTIR) spectroscopy and by a diffuse reflectance technique. If the drilling fluid contains dissolved salts, the weight $M_e$ of such salts is determined, and the weight fraction of solids $W_s$ is corrected accordingly.

The principles of IR spectroscopy are well know, and in general the technique requires the sample being analysed to be "mounted" on or within an IR-transparent carrier. Thus, for example, in conventional transmission spectroscopy the sample is pasted with NUJOL (or some similar paste) and supported between two rocksalt (sodium chloride)plates, while for conventional reflectance spectroscopy the sample is incorporated into a salt powder. Indeed, this latter technique is useable with advantage in the method of the invention, so that the preparation of the powder for infrared analysis includes the mixing of a known weight of dried drilling fluid solids with a halide salt to form a mixture, and grinding the mixture until the particle size of the solids is no more than 2 microns to obtain the desired powder. The halide salt is preferably potassium bromide or sodium chloride.

A reflectance spectrum obtained from a salt/sample powder admixture can be perfectly satisfactory. However, in a reflectance method of this type a high proportion of the returned IR energy has in fact undergone transmission through the surface "layers" of the sample powder, and recent work has shown that, because of the relatively similar refractive indices of the materials involved, one result of effectively incorporating the sample solids within the salt is for refractive effects to mask the weaker signals produced by some of the less plentiful sample components. It has now been found that a rather different—and in some ways markedly superior—spectrum can very usefully be obtained by analysing the sample powder "raw" (as it were) rather than incorporated with a halide salt. Some comparative results relating to this are given and discussed hereinafter.

Whether the spectroscopy is carried out by transmission or by reflectance and if the latter whether with the sample incorporated with a halide salt or not, the interpretation of the concentration of the products is preferably achieved by first obtaining the infrared spectra of known compositions of the drilling fluid products and by generating a calibration model from those spectra.

The following description of the invention is accompanied by drawings in which FIGS. 1 and 2 relate to a first example and FIGS. 3 and 4 relate to a second example:

FIG. 5($b$) is a calibration curve for XC;

PRELIMINARY SAMPLING, MATHEMATICAL AND SPECTROSCOPIC CONSIDERATIONS

Figure 1:
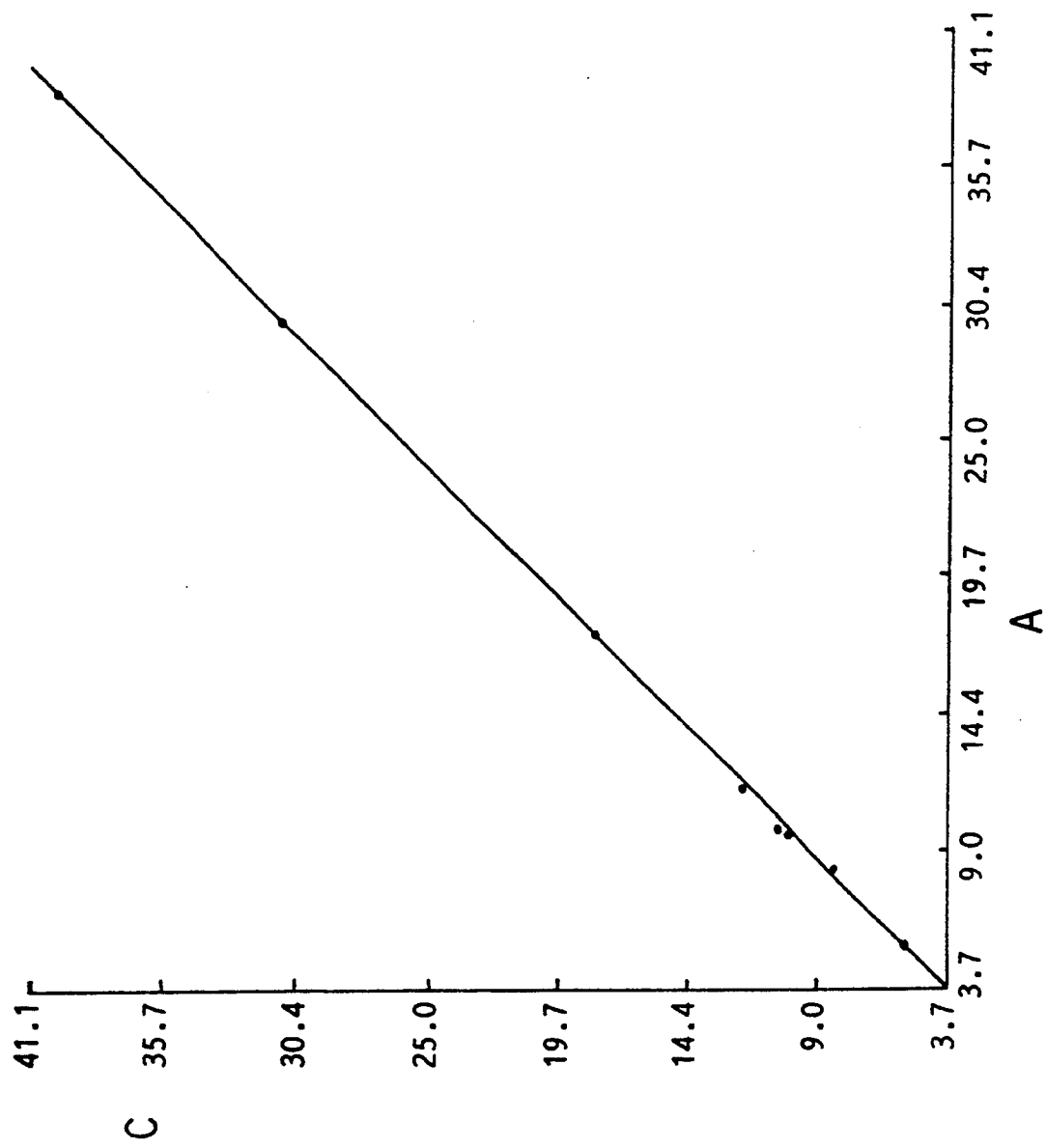
FIG. 1 shows the fit of a calibration model to calibration samples for different concentrations in carboxymethyl cellulose polymer (CMC), for a mud containing CMC and bentonitc.

A sample of drilling fluid is taken from the drilling fluid circulating at the surface, preferably in the mud pit (so as to obtain information on the drilling mud being circulated downhole through the drill string), and/or downstream of the shale shaker but upstream of the mud pit (so as to obtain information on the drilling fluid returning to the surface from the borehole).

The weight $M_m$ of an accurately known volume $V_m$ of mud sample is measured, which determines the mud density $d_m$ $$d_m = \frac{M_m}{V_m} \qquad (1)$$

A known weight of the mud is dried to constant weight in an oven, or (more conveniently) an infrared drier balance, at a temperature in excess of 100° C. but below temperatures which cause degradation of the polymers in the mud (about 200° C.). An infrared drier balance is preferred both because the mud sample may be smaller than the ones dried in an oven and because a direct reading of the solids weight is obtained. The weight of water $M_w$ lost on drying the mud enables the weight fraction of solids $W_s$ in the mud to be determined by:

$$W_s = \frac{M_m - M_w}{M_m} \qquad (2)$$

If the mud flitrate contains dissolved salts (electrolyte), the mud weight $M_m$ is equal to $M_w + M_s + M_e$, in which $M_s$ and $M_e$ are the weight of the solids and the salts, respectively. Then a corrected solids content can be obtained from:

$$W_s = \frac{M_m - M_w - M_e}{M_m} \qquad (3)$$

The weight of $M_e$ can be conveniently determined from the measurement of the concentration $c_i$ of ions in solution using a suitable analytical technique, eg ion chromatography:

$$M_e = \frac{M_w}{d_w} \sum_i \frac{c_i}{M_i} \qquad (4)$$

where $d_w$ is the density of water and $M_i$ is the molar mass of ion$_i$. Such a method is, for example, described in EP Patent Application 0,316,985. The polymers contained in the mud are mixed with the solids after drying out the mud sample, and for the purposes of analysis, can be considered solid components.

The dried mud solids and polymers are prepared for quantification using infrared spectroscopy. Firstly, an accurate weight of dried mud solids and polymers are mixed with the halide salt (such as potassium bromide or sodium chloride) to form a mixture of the mud solids and halide salt, the chosen concentration of mud solids being about 5 weight percent. The halide salt decreases the difference of refractive indexes between the air and the mixture, and therefore decreases the loss of infrared radiation by reflection on the solids. The mixture is ground in a ball mill or pestle and mortar, preferably made of agate or corundum to minimise contamination from the material of the mill during grinding, to form a powder the particle size of which is below 10 microns, ie comparable to the wavelength in the mid-infrared range. Such a particle size can be achieved within a few minutes using a small grinding mill —eg, a Wig-L-Bug microniser manufactured by Crescent Dental Manufacturing Company of the USA.

A sample of the powdered mud solids in the finely ground halide salt is placed in a diffuse reflectance cell, and the spectrum collected by an infrared spectrometer, preferably a Fourier transform infrared spectrometer. The equivalent transmission spectrum can be obtained by performing the Kubelka-Munk transform on the raw reflective spectrum data. This transform is described for example in the book "Reference Spectroscopy" by G Kortüm, a Springer-Verlag Publication 1969. Such a transform is convenient only but not essential for the quantification. The diffuse reflectance spectrum corresponds to infrared radiation emitted by the solids molecules following their absorption of the radiation emitted by the infrared source of the spectrometer.

An alternative and better-known technique to collect the infrared spectrum of the mud solids is by direct transmission. The mixture of mud solids and halide salt is pressed into a solid disc (pellet) using a press capable of exerting loads of up to 10tonnes. For the quantification of mud solids the diffuse reflectance technique is preferred for the following reasons:

- diffuse reflectance is a more rapid technique, and avoids the manufacture of halide pellets;
- overtone and weaker bands in the infrared spectrum are often more prominent in diffuse reflectance than in direct transmission; and
- direct transmission techniques often give rise to intense absorption bands in the infrared spectrum which may not be suitable for use in linear quantitative techniques.
- larger sample weights are used in the diffuse reflectance technique, typically being in the range of 0.04–0.4 g compared with sample weights of typically 0.004 g used in direct transmission techniques. The analytical problems of obtaining accurate weights and representative samples is therefore reduced.

The two last mentioned reasons may prevent the whole transmission spectrum from being used to quantify the components in the mud solids. In contrast, the whole diffuse reflectance spectrum is available for quantitative analysis—and the improvement is even more marked where a reflectance spectrum is obtained from a sample that has not been incorporated in a halide salt.

The diffuse reflectance spectrum of the recovered mud solids can be interpreted quantitatively using a number of techniques, including the Beer-Lambert law. In accordance with this law, there is a linear relationship between the diffuse reflectance—or the absorbance—of a product and its concentration at a single, fixed frequency, and the spectrum of a mixture can be analysed in terms of a characteristic value of frequency for each of its individual components. However, a multivariate statistical technique, which uses the absorbance at a number of wavelengths, is preferred since a mixture of several components often results in marked deviations in the Beer-Lambert law. The spectrum of a mixture can be considered to be a linear combination of those of the pure components, and calibrations must be developed from the spectra of such mixtures. Multivariate statistical techniques can be used to generate a calibration model of the dried mud solids; the model essentially consists of a regression (or partial regression) of the spectral and concentration data sets of standards of accurately known compositions. Examples of such multivariate techniques are multiple linear regression, principal components analysis and partial least squares path modelling. This last technique is preferred and is described in the book "Multivariate Calibration" by H Martens and T Naes, a Wiley Publication, 1989. An example of a computer programme to perform the partial least squares regression is the well-known UNSCRAMBLER software, developed at the Norwegian Food Research Institute and described in the journal "Chemometrics and Intelligent Laboratory Systems", Volume 2, pages 239—243, 1987.

The quantity or concentration of products in the original (undried) mud can be calculated as follows. The spectroscopic analysis gives the concentration of each product in the mud solids, preferably as a weight fraction. For component $i$ of weight fraction $w_i$ in the mud solids, the total weight fraction $W_i$ in the mud is $$W_i = w_i W_s, \quad (5)$$

which gives the weight of component $i$ per unit weight of mud, such as kilogram of component per kilogram of mud. For a mud density $d_m$, the actual concentration is $$c_i = w_i W_s d_m \quad (6)$$

where the density $d_m$ has the same units as the concentration $c_i$ (eg, kg/m3).

It is preferred to determine the concentration of the products in the mud, but any value representative or characteristic of the concentration could be determined within the scope of the invention.

The present invention is also useful for assessing the working condition of the mud solids equipment, such as the hydrocyclones, mud cleaners and centrifuges. One way to do this is to monitor the variation in the concentration or quantity of one of the products treated by the mud solids equipment, such as barite (this supposes that any loss of product, and therefore any decrease in the measured concentration, is due to the mud solid equipment only). Another way, which is preferred, is to determine the concentrations or quantities of the product from mud samples taken upstream and downstream of the mud surface equipment (for example, at the mud exit of the shale shaker and in the mud pit), and to compare the upstream and downstream concentrations. The result of the comparison indicates the working condition of the equipment, such as how much barite is extracted by the equipment. Obviously the assessment of the working condition can be made for one piece of equipment only, such as the mud cleaner.

EXAMPLE 1

Quantification of Various Components in a Water-based Mud

A first example is presented to show the principles of the method and the accuracy which can be achieved by the technique.

The water-base mud to be analysed consisted of a mixture of bentonite and a low-viscosity carboxymethyl cellulose of varying concentrations. A calibration model was constructed from a series of 8 standards with bentonite concentration in the dried solids in the range 0.6033–0.9477 weight fraction. Therefore the polymer concentration in the dried solids was in the range 0.0523–0.3967 (the sum of the weight fractions of the polymer and bentonite being equal to 1).

For each standard whose composition was accurately known, the diffuse reflectance spectrum was collected using the Fourier transform infrared (FTIR) technique. A regression model of absorbance as a function of concentration was generated from the diffuse reflectance FTIR spectra, using a partial least squares path modelling algorithm. FIG. 1 shows the concentration of polymer C calculated from the calibration model as a function of the actual concentration A of samples. The fit of the calibration model to the calibration samples is clearly apparent: the correlation coefficient of the least squares best fit is 0.999.

Figure 2:
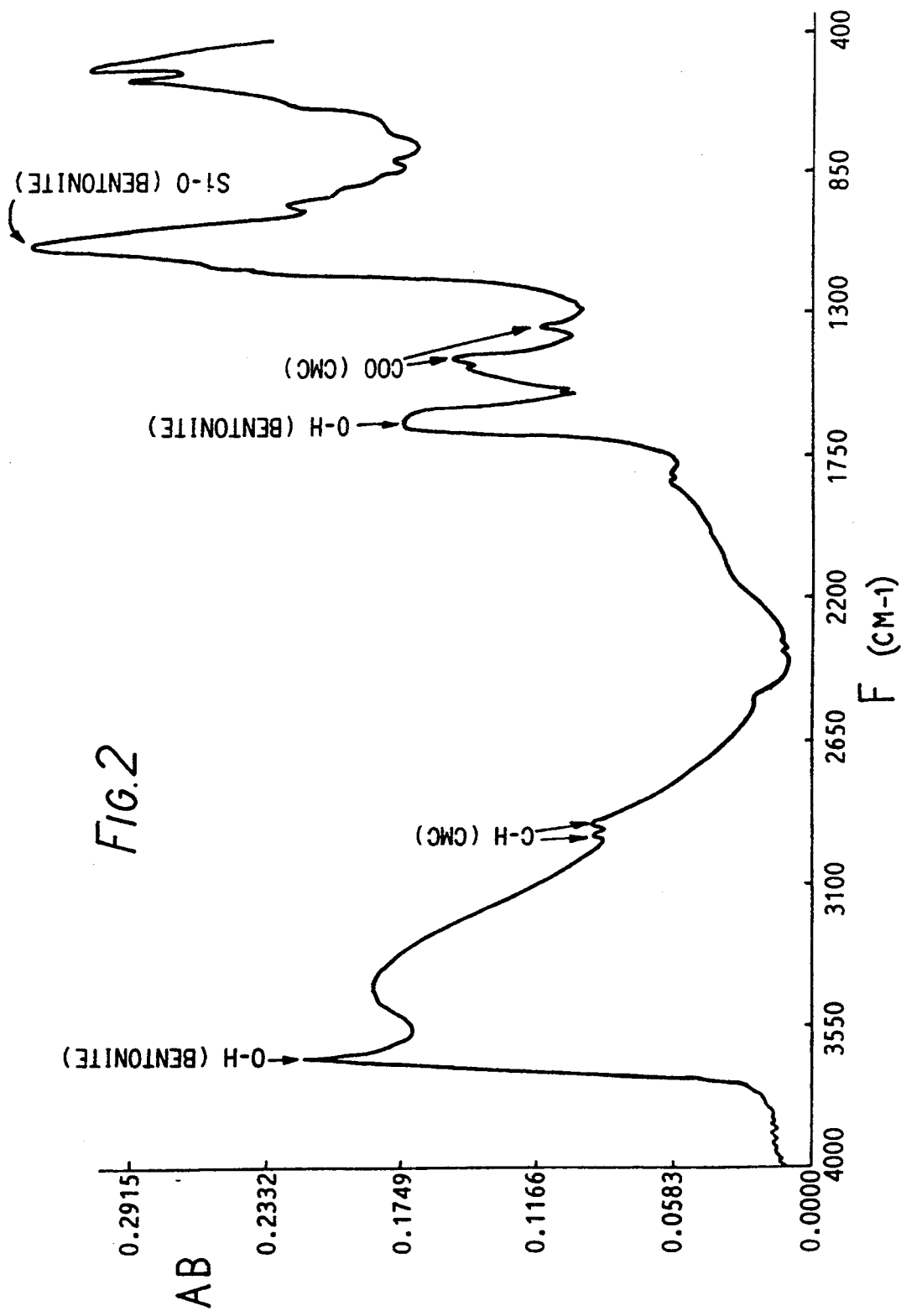
FIG. 2 is an example of an FTIR spectrum of a calibration mud sample containing bentonite and carboxymethyl cellulose (CMC)

An equivalent plot can also be obtained from bentonite with samples of known bentonite concentration. FIG. 2 shows an example of the FTIR spectrum of a calibration sample, displaying the absorbance AB of the solids bentonite and polymer as a fraction of the wavenumber F (in cm$^{-1}$) of the infrared radiation. The absorbance values were obtained by performing the Kubelka-Munk transform on the raw diffuse reflectance spectrum. The absorption bands due to both bentonite and polymer are clearly visible, and have been marked in the Figure by their characteristic groups of molecules —O—H and Si—O for bentonite, and C—H and COO for carboxymethyl cellulose (CMC).

The calibration model was tested on 3 water-based mud samples of accurately known bentonite and polymer content, and the results are summarised in Table 1. The solids content of the 3 muds was calculated from the accurately known weights of bentonite and polymer used to make the mud. The measured solids content from the infrared spectra of the 3 dried mud solids samples were collected by the diffuse reflectance technique, and subsequently processed through the multivariate calibration model to determine the weight fractions of bentonite and polymer in the samples. Table 1 shows good agreement between the actual and measured weight fraction $w_i$ of bentonite and polymer in the mud solids which, together with the known solids content of the mud and mud density, were convened to actual concentrations by use of eqn [6]. The polymer concentration was measured to within ±10% of the actual concentration.

EXAMPLE 2

Quantification of Barite and Bentonire in a Water-based Mud

The second example shows the application of a calibration model to quantify the barite and bentonite content of a water-based mud with contaminating drilled solids, ie, drilled "fines" which have become associated with the mud solids.

A calibration model was based on a nominal composition of 60 grams of bentonite and 340 grams of barite per liter of mud; the weight fraction solids content was 0.3086 (30.86 weight percent). The dried mud solids therefore had a nominal composition of weight fraction 0.85 barite and 0.15 bentonite. A calibration model was constructed such that the barite content of the dried mud solids could vary between 0.75 and 0.90 while the bentonite content covered the range 0.09–0.20. In addition, the mud was contaminated with drilled calcite and quartz fines which could each vary between 0 and 0.1 weight fraction. The calibration model thus covered the following compositions:

| | |
|---|---|
| barite: | 0.75–0.90 |
| bentonite: | 0.09–0.20 |
| calcite: | 0–0.10 |
| quartz: | 0–0.10 |

Figure 3:
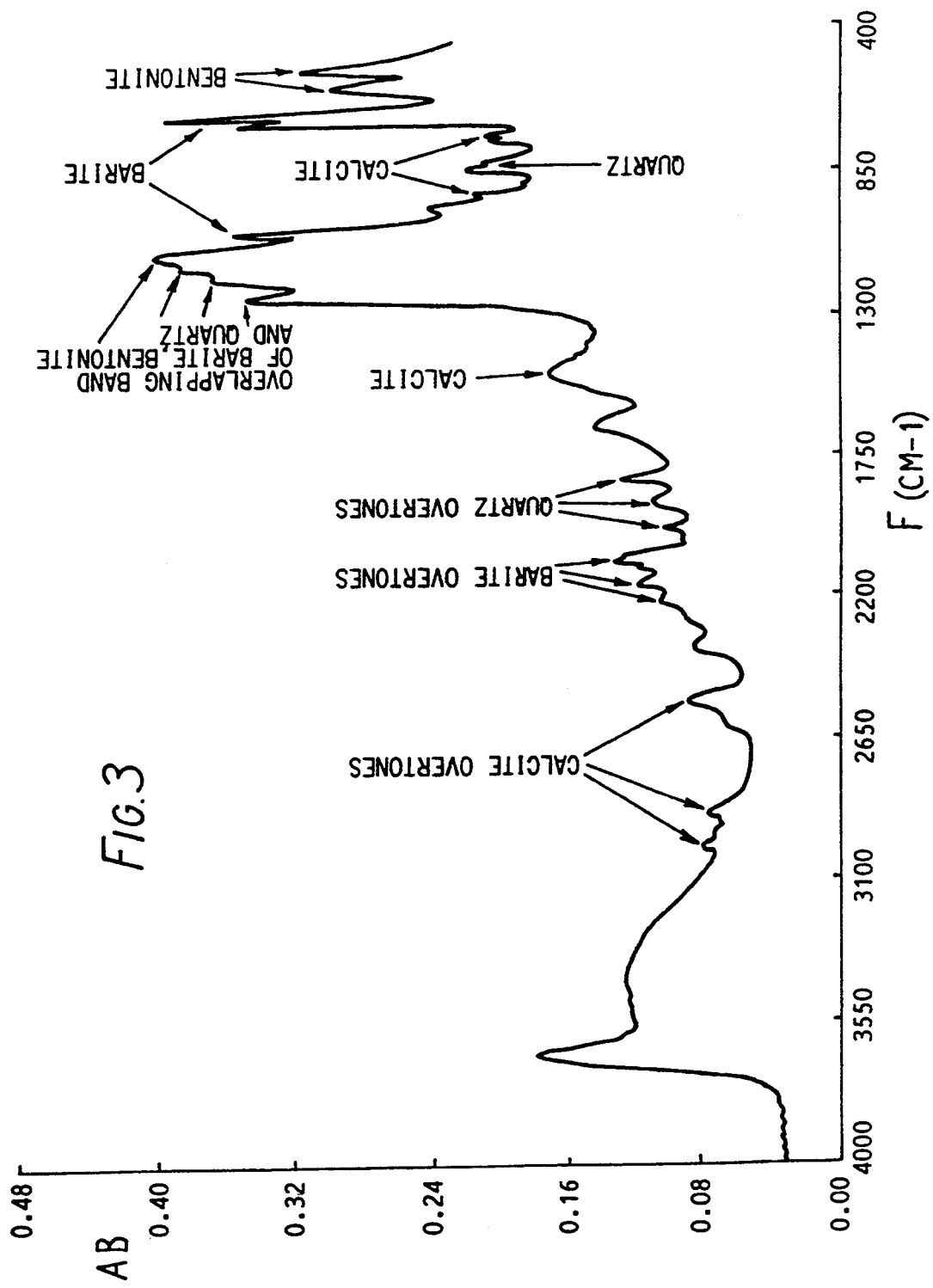
FIG. 3 is an example of an FTIR spectrum of a calibration mud sample containing barite, bentonite, calcite and quartz.

A calibration model was constructed from 17 standards which covered this range of mud solids composition. The FTIR spectrum of each standard was collected by diffuse reflectance. FIG. 3 shows the FTIR spectrum of a calibration standard which consisted of absorbance AB versus wavenumber F (in $cm^{-1}$), for the following mud composition:

| product: | barite | weight fraction: | 0.750 |
|---|---|---|---|
| | bentonite | | 0.110 |
| | calcite | | 0.070 |
| | quartz | | 0.070 |

Figure 4:
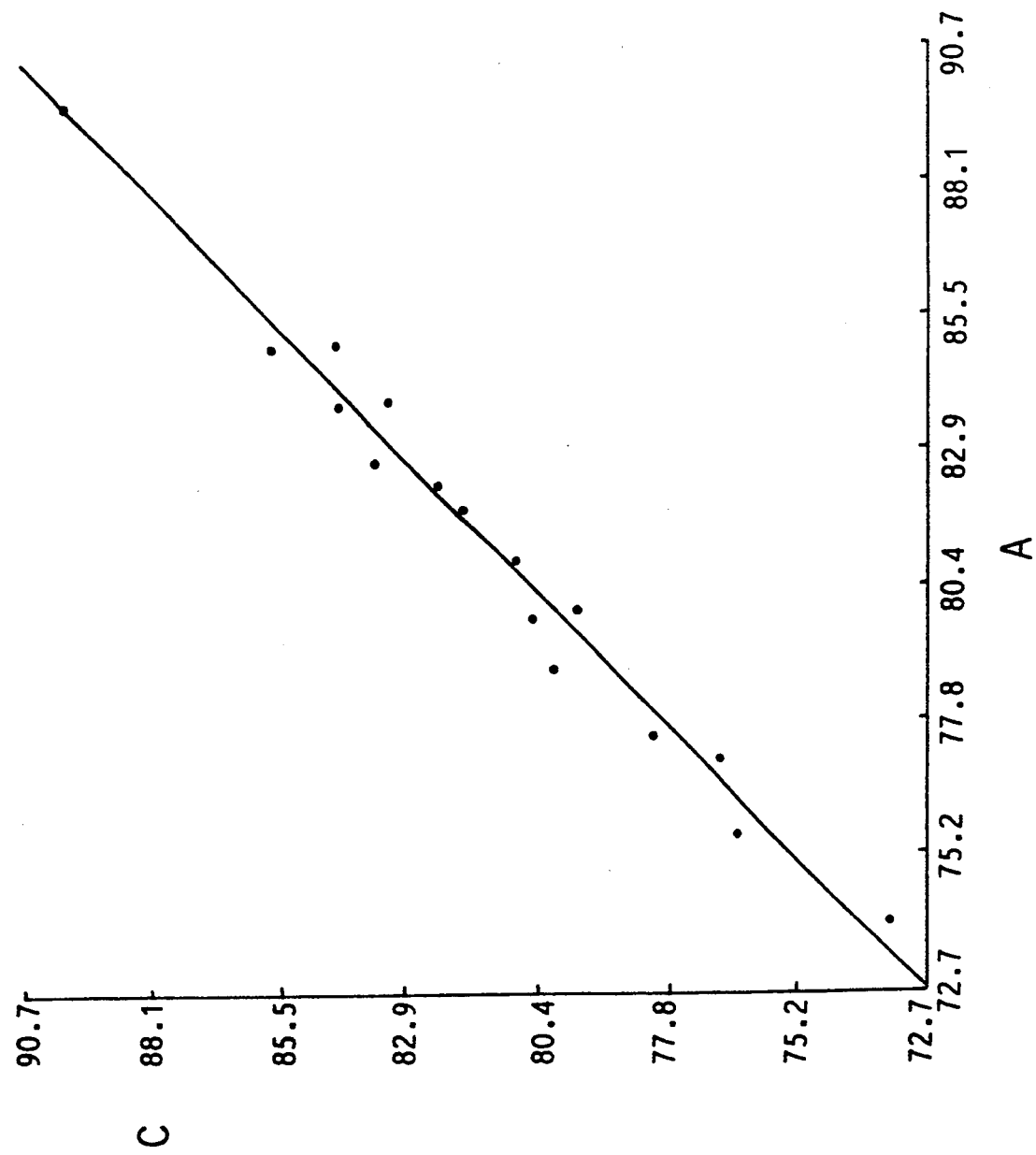
FIG. 4 shows the fit of a calibration model to calibration samples for different concentration in barite, for a mud containing barite, bentonite, calcite and quartz.

On FIG. 3, the peaks have been identified, successively from high to low values of wavenumber F, as calcite overtones, barite overtones, quartz overtones, calcite, an overlapping band of barite, bentonitc and quartz, barite, calcite, quartz, calcite, barite, and finally bentonitc. The calibration model was generated by a partial least squares regression of the spectral and composition data. FIG. 4 represents the calculated values C of barite concentration, calculated from the calibration model, versus the actual values A. The fit of the calibration model values to the calibration samples is clearly apparent.

Three mud samples of accurately known composition were then analysed to demonstrate the accuracy of the model. The results are shown in Table 2, where the composition of the mud solids as determined by infrared spectroscopy are compared to their known values. There is a good agreement between the measured and actual values.

In the above examples, the spectra were obtained by Fourier transform infrared spectroscopy—ie for each spectrum an interferogram was first obtained, and the interferogram data were then convened from the time domain into the frequency domain by a Fourier transform technique. These operations were done automatically in the FTIR spectrometer, and were not apparent to the operator. It should first be remarked that other techniques, other than the Fourier transform technique, exist to convert data from the time to frequency domain, such as for example the so-called Hadamard and maximum entropy techniques. Furthermore, the analysis of the interferogram does not necessarily include the conversion of the time data into the frequency domain. A direct regression method could be used, in which the interferogram data could be compared directly with reference data obtained from the spectra of reference samples. An instance of such a direct method is for example given in the article "Partial Least Squares Quantitative Analysis of Infrared Spectroscopy Data" in Applied Spectroscopy, 1988, Volume 42, Number 2, page 235. The present invention is therefore not limited to the use of a Fourier transform technique.

Examples 1 and 2 relate to reflectance spectra obtained from a sample of dried drilling mud and powdered in admixture with a halide salt. The following two examples serve to demonstrate that, for certain water-based drilling fluid formulations, a more accurate quantification of drilling fluid products may be obtained from a calibration model constructed from spectra obtained from crushed "raw" mud solids powders rather than from mud solids powders dispersed in a halide salt.

EXAMPLE 3

Quantification of Five Components in a Salt-Saturated Water-Based Mud

The water-based mud to be analysed contains five components dispersed in a salt solution. The five components to be quantified are simulated drilled clay solids (OCMA grade which is mainly composed of kaolinire), an asphaltene product (Solrex), and three polymeric products, namely starch, partially hydrolysed polyacrylamide (PHPA), and xanthan gum (XC).

20 standard muds were prepared with the concentration of each component varying independently within the ranges listed below:

| | |
|---|---|
| OCMA | 97.45–163.20 g/l |
| Soltex | 5.87–10.88 g/l |
| starch | 7.91–11.73 g/l |
| PHPA | 0.99–2.48 g/l |
| XC | 0.99–3.00 g/l |
| NaCl | 244 g/l |
| NaOH | 3 g/l |

Dried mud solids powders produced from each of the 20 standard muds contain component weight fractions within the ranges listed below:

| | |
|---|---|
| OCMA | 0.2682–0.3776 |
| Soltex | 0.0153–0.0279 |
| starch | 0.0114–0.0312 |
| PHPA | 0.0026–0.0063 |
| XC | 0.0026–0.0075 |
| NaCl | 0.5553–0.6723 |
| NaOH | 0.0071–0.0085 |

Evaporated salts account for between 56 and 68 wt. % of the dried mud solids; sodium chloride, which accounts for between 55.5 and 67.2 wt. % of the dried mud solids, produces a non-absorbing diffusely reflecting matrix, so that the FTIR spectrum for each crushed "raw" mud solids powder is donfinated by the spectrum for OCMA. Since the sodium chloride matrix is nonabsorbing, the OCMA component accounts for between 82 and 87 wt. % of the absorbing components. The weight fraction of the two polymefic products, (PHPA and XC) in the dried mud solids is very low, ranging between 0.0026 and 0.0075 (note that the PHPA and XC concentrations vary by factors of 2.4 and 2.9 across the range).

The following data serve to demonstrate that, for this particular mud formulation, a more accurate quantification of PHPA and XC is obtained by constructing a calibration model using crushed "raw" undiluted mud solids powders rather than by using crushed mud solids powders dispersed in a halide salt.

Use of a Calibration Model Using Crushed Mud Solids Dispersed in Potassium Bromide Each mud solids/potassium bromide mixture was obtained by mixing 0.06 g mud sol;,ds powder with 0.54 g potassium bromide; such a dilution reduces the absolute weight fractions of PHPA and XC to 0.00026–0.00075. Correlation coefficients for the calibration model obtained are listed below:

| Component | Calibration coefficient | Comment |
|---|---|---|
| OCMA | 0.763 | Acceptable |
| Soltex | 0.990 | Acceptable |
| starch | 0.715 | Acceptable |
| PHPA | 0.367 | Too low |
| XC | 0.599 | Too low |

Whilst the calibration coefficients for the "major" components (OCMA, Soltex and starch) indicate that the calibration model may be used for their quantification, the corresponding coefficients for the "minor" components (PHPA and XC) are Ix,or. Due to both the very low absolute weight fraction of PHPA and XC in the mud solids/potassium bromide mixtures and the predominance of OCMA amongst the absorbing components, the deconvolution of spectral information specific to the PHPA and XC components may be approaching a detection limit for their quantification. Effectively, spectral variance due to the PHPA and XC components cannot be adequately correlated with respect to their concentration variance.

Figure 5B:
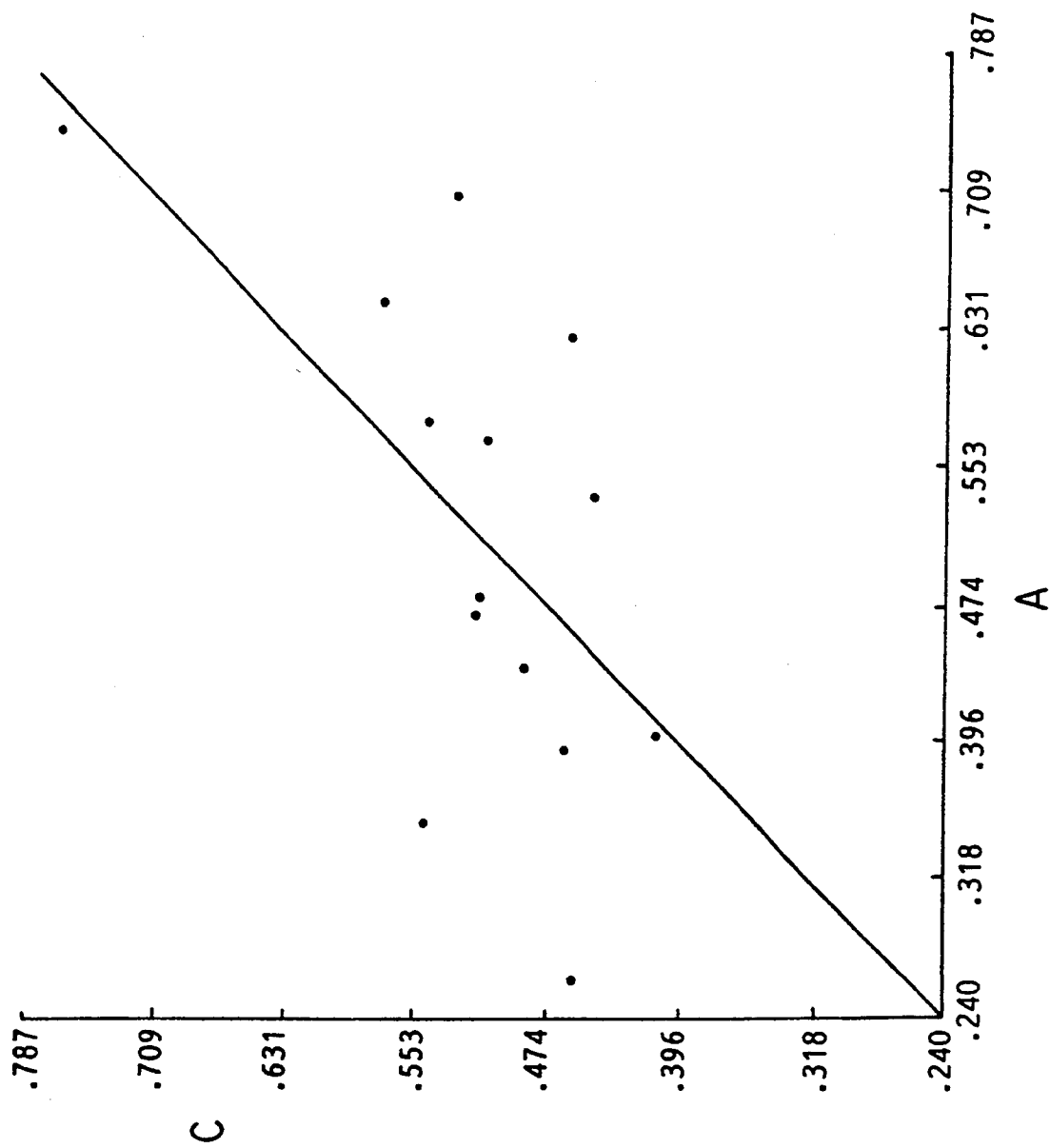
FIG. 5($a$) is a calibration curve for PHPA.

Calibration curves for PHPA and XC are shown in FIGS. 5a and 5b. Clearly, whatever the actual concentration of PHPA in the range 0.245–0.645 wt. % in an unknown dried mud solids powder, the model will predict a calculated concentration in the range 0.375–0.541 wt. % (refer to FIG. 5a). Similarly, whatever the actual concentration of XC in the range 0.240–0.713 wt. % in an unknown dried mud solids powder, the model will predict a calculated concentration in the range 0.408–0.577 wt. % (refer to FIG. 5b); it is notable that the model will predict a near correct XC concentration (0.768 wt. %) for standard "1" which has the highest actual XC concentration at 0.75 wt. %. The latter result may indicate that the detection limit for an accurate quantification of XC in a dried mud solids powder, using a calibration model constructed from spectra for 10 wt. % mud solids powder 90 wt. % potassium bromide mixtures, lies in the XC concentration range 0.713–0.768 wt. %; such a detection limit corresponds to a whole mud XC concentration of 3 g/l.

The results for a series of six test muds calculated using the calibration model constructed from spectra for mud solids dispersed in potassium bromide are shown in Table 3. The data indicate that the "major" components, OCMA, Solrex and starch are quantified within relative accuracies of ±4.8%, ±4.7% and ±8.7% respectively. However, the "minor" components, PHPA and XC are quantified within relative accuracies of ±14.5% and ±24.8% respectively.

Use of a Calibration Model Using Crushed "Raw" Undiluted Mud Solids Powders

Correlation coefficients for the calibration model are listed below:

| OCMA | 0.999 |
|---|---|
| Soltex | 0.946 |
| starch | 0.999 |
| PHPA | 0.986 |
| XC | 0.982 |

Figure 6A:
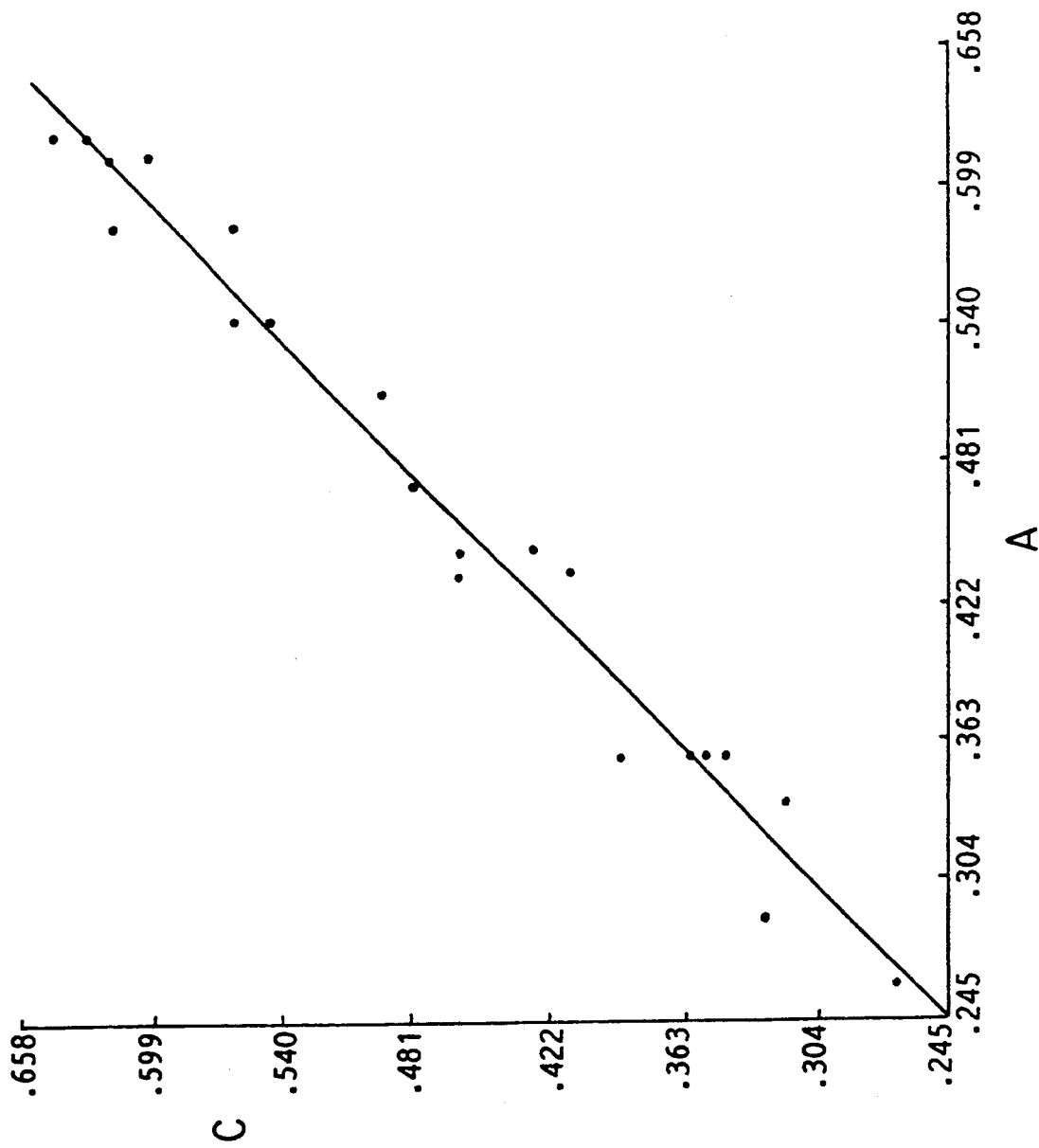
FIG. 6($a$) is a calibration curve for PHPA for an undiluted powder.
FIG. 6(b) is a calibration curve for XC for an undiluted powder.
Figure 6B:
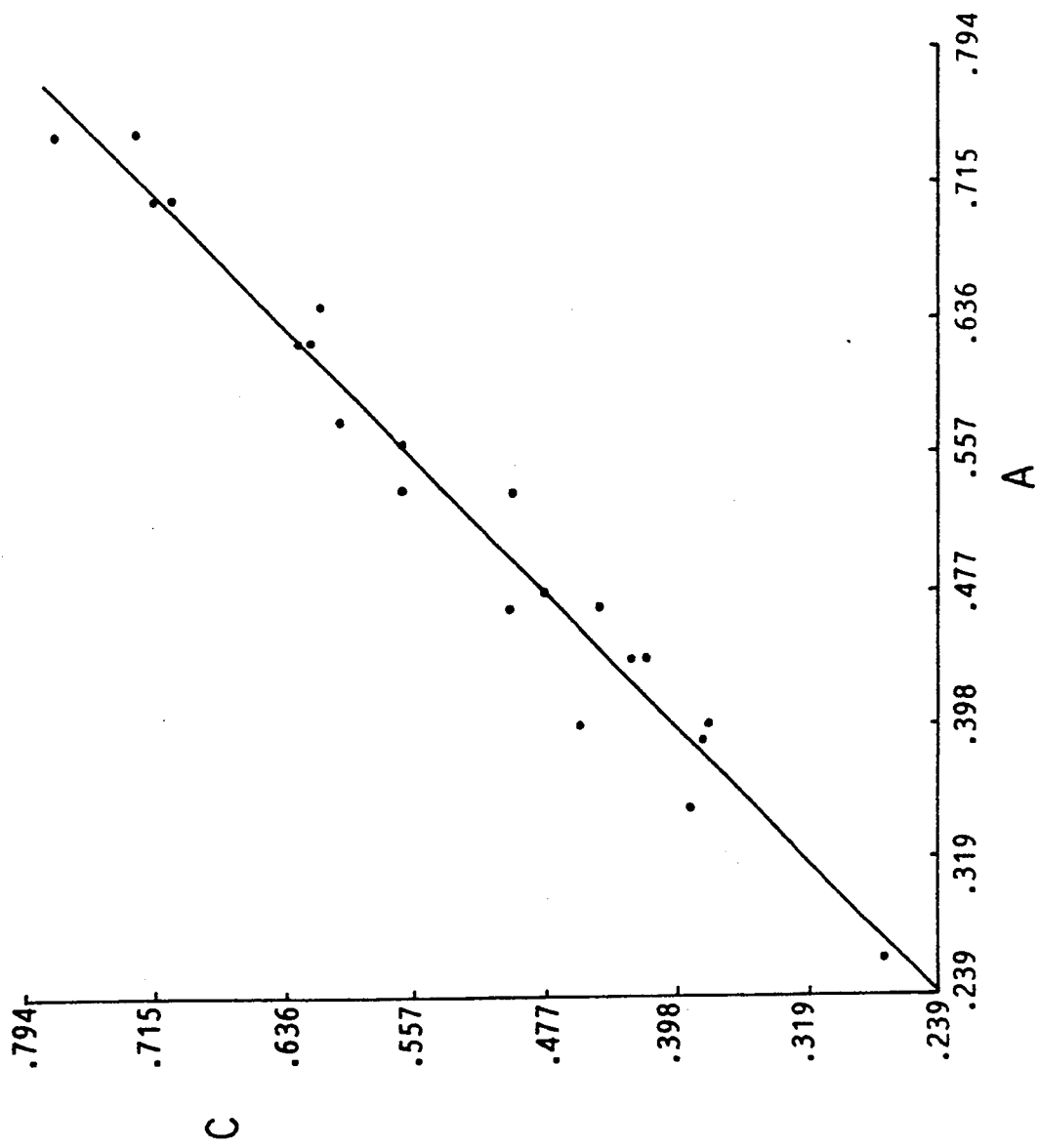

The above calibration coefficients for each of the 5 components are significantly higher than the coefficients quoted for the model constructed using mud solids powders diluted with potassium bromide. Calibration curves obtained for PHPA and XC for the model constructed using "raw" undiluted mud solids powders are shown in FIGS. 6a and 6b; clearly, the calibrations have been significantly improved as compared to the model constructed using mud solids powders diluted with potassium bromide (cf. FIGS. 5a and 5b).

The results for the series of six test muds calculated from the calibration model constructed using "raw" undiluted mud solids powders are given in Table 4. The data indicate that the "major" components, OCMA, Soltex and starch are quantified within relative accuracies of ±4.2%, ±10.7% and ±6.8% respectively; a comparison with the results for the same test muds calculated front the calibration model constructed using mud solids powders diluted with potassium bromide (refer to Table 3) leads to the conclusion that dilution in potassium bromide will significantly increase the accuracy for determination of Soltex but will not significantly increase the accuracy for determination of OCMA and starch. The data given in Table 4 indicate that the "minor" components, PHPA and XC are quantified within relative accuracies of ±13.5% and ±12.0% respectively; a comparison with the results for the same test muds calculated from the calibration model constructed using mud solids powders diluted with potassium bromide (refer to Table 3) leads to the conclusion that dilution in potassium bromide will significantly reduce the accuracy for determination of PHPA and XC.

EXAMPLE 4

Quantification of Five Components in a Freshwater Based Mud

The water based mud to be analysed contains five components dispersed in deionised water. The five components are Bentonitc, low viscosity grade carboxymethyl cellulose (CM-CLV), xanthan gum (XC), calcite, and barite.

20 standard muds were prepared with the concentration of each component varying independently within the ranges listed below:

| Bentonite | 19.72–69.91 g/l |
|---|---|
| CMC-LV | 3.91–15.98 g/l |
| XC | 0.81–4.25 g/l |
| calcite | 18.46–37.19 g/l |
| barite | 90.57–230.05 g/l |

Dried mud solids produced from each of the 20 standard muds contain component weight fractions within the ranges listed below:

| Bentonite | 0.0716–0.3039 |
|---|---|
| CMC-LV | 0.0169–0.0681 |
| XC | 0.0026–0.0203 |
| calcite | 0.0982–0.1595 |
| barite | 0.4849–0.7542 |

Barite accounts for between 48 and 75 wt. % of the dried mud solids; XC covers the low concentration range of 0.26 and 2.03 wt %. In contrast to Example 3, the following data serve to demonstrate that for this particular mud formulation, a significantly more accurate quantification of CMC-LV and XC is obtained by constructing a calibration model using crushed mud solids dispersed in potassium bromide rather than by using crushed "raw" undiluted mud solids powders.

Use of a Calibration Model Using Crashed Mud Solids Dispersed in Potassium Bromide Each mud solids/potassium bromide mixture was obtained by mixing 0.06 g mud solids powder with 0.54 g potassium bromide; such a dilution reduces the absolute weight fraction of XC to 0.00026–0.00203 (note that XC concentration varies by a factor of 7.8 across the range). Correlation coefficients for the calibration model obtained are listed below:

| Component | Calibration coefficient |
|---|---|
| Bentonite | 0.997 |
| CMC-LV | 0.997 |
| XC | 0.931 |
| calcite | 0.981 |
| barite | 0.988 |

Calibration coefficients for each of the five components indicate that the model may be used for their accurate quantification. Results for a series of six test muds calculated from the model are given in Table 5. The data indicate that the "major" components, barite, bentonite and calcite are quantified within relative accuracies of ±1.3%, ±6.0% and ±2.0% respectively; the "minor" components, CMC-LV and XC are quantified within relative accuracies of ±10.8% and ±9.8% respectively.

Use of a Calibration Model Using Crushed "Raw" Mud Solids Powders

Correlation coefficients for the calibration model are listed below:

| Bentonite | 0.929 |
|---|---|
| CMC-LV | 0.801 |
| XC | 0.993 |
| calcite | 0.814 |
| barite | 0.990 |

Calibration coefficients for each of the five components indicate that the model may be used for their quantification; however, the coefficients are generally lower than those achieved using mud solids powders dispersed in potassium bromide. Results for the same series of six test muds calculated using the model constructed using "raw" mud solids powders are given in Table 6. Whilst the "major" components, barite, bentonite and calcite are quantified within relative accuracies of ±1.7%, ±9.5% and ±4.8% respectively, the "minor" components, CMC-LV and XC are less well quantified within relative accuracies of ±9.7% and ±20.5% respectively.

A comparison of the results given in Tables 5 and 6 leads to the conclusion that a dilution of the mud solids in potassium bromide will significantly increase the accuracy for determination of Bentonire, CMC-LV, XC and calcite in this particular water based mud formulation.

TABLE 1

|  |  |  | TEST MUD BATCH No | | |
|---|---|---|---|---|---|
|  |  |  | 1 | 2 | 3 |
| SOLIDS CONTENT | | Actual | 4.82 | 2.77 | 2.93 |
| (Wt. %) | | Measured (IR dryer bal.) | 4.89 | 2.75 | 2.97 |
| QUANTIFICATION OF COMPONENTS | | | | | |
| CMC | MUD SOLIDS | Actual | 9.25 | 12.42 | 29.74 |
|  | (Wt. %) | Measured (FTIR) | 9.75 | 11.20 | 30.50 |
|  | WHOLE MUD | Actual | 4.53 | 3.47 | 8.75 |
|  | (g/l) | Measured | 4.91 | 3.13 | 9.21 |
| BENTONITE | MUD SOLIDS | Actual | 90.75 | 87.58 | 70.26 |
|  | (Wt. %) | Measured (FTIR) | 90.25 | 88.80 | 69.50 |
|  | WHOLE MUD | Actual | 44.46 | 24.43 | 20.67 |
|  | (g/l) | Measured | 45.42 | 24.82 | 20.99 |

TABLE 2

|  |  | TEST MUD BATCH No | | |
|---|---|---|---|---|
|  |  | 1 | 2 | 3 |
| DENSITY $d_m$ (g/l) | | 1.294 | 1.294 | 1.298 |
| SOLID WEIGHT % $W_s$ | | 0.3120 | 0.3093 | 0.3077 |
| BARITE | | | | |
| WEIGHT % MEASURED (FTIR) | | 75.9 | 80.2 | 87.7 |
| CONCENTRATION C | Measured (FTIR) | 306.4 | 321.0 | 350.3 |
| (g/l) | Actual | 302.6 | 318.4 | 354.2 |
| WEIGHT % MEASURED (FTIR) | | 9.0 | 16.1 | 9.9 |
| CONCENTRATION C | Measured (FTIR) | 36.3 | 64.4 | 39.5 |
| (g/l) | Actual | 36.4 | 65.7 | 36.0 |
| WEIGHT % MEASURED (FTIR) | | 10.0 | 2.1 | 1.1 |
| CONCENTRATION | Measured (FTIR) | 40.4 | 8.4 | 4.4 |
| (g/l) | Actual | 40.3 | 8.0 | 4.6 |
| WEIGHT % MEASURED (FTIR) | | 6.0 | 1.7 | 1.1 |
| CONCENTRATION C | Measured (FTIR) | 24.2 | 6.8 | 4.4 |
| (g/l) | Actual | 24.4 | 8.2 | 4.6 |

TABLE 3

Results for 6 test muds calculated using calibration model constructed using mud solids diluted in potassium bromide.

| | | | TEST MUD BATCH NO. | | | | | |
|---|---|---|---|---|---|---|---|---|
| | | | 1 | 2 | 3 | 4 | 5 | 6 |
| SOLIDS | | Actual | 33.20 | 29.29 | 31.29 | 32.94 | 32.74 | 30.52 |
| CONTENT | | Measured | 32.21 | 29.61 | 30.99 | 32.46 | 32.25 | 30.30 |
| (Wt. %) | | *Difference | −0.99 | +0.32 | −0.30 | −0.48 | −0.49 | −0.22 |
| | | †Relative difference | −3 | +1 | +1 | −1 | −1 | −1 |
| QUANTIFICATION OF COMPONENTS | | | | | | | | |
| OCMA | Whole Mud | Act. | 137.74 | 97.45 | 112.56 | 141.74 | 139.31 | 100.42 |
| | (g/l) | Meas. | 129.14 | 102.43 | 116.92 | 134.02 | 144.69 | 105.29 |
| | | Diff. | −8.6 | +4.98 | +4.36 | −7.72 | +5.38 | +4.87 |
| | | Relative difference | −6 | +5 | +4 | −5 | +4 | +5 |
| Soltex | Whole Mud | Act. | 9.34 | 6.35 | 10.76 | 6.37 | 6.81 | 9.32 |
| | (g/l) | Meas. | 8.80 | 6.53 | 10.72 | 7.06 | 7.10 | 8.95 |
| | | Diff. | −0.54 | +0.18 | −0.04 | +0.69 | +0.29 | −0.37 |
| | | Relative difference | −6 | +3 | 0 | +11 | +4 | −4 |
| Starch | Whole Mud | Act. | 10.00 | 7.92 | 9.14 | 11.50 | 11.13 | 9.36 |
| | (g/l) | Meas. | 8.72 | 8.53 | 9.26 | 10.19 | 9.42 | 8.91 |
| | | Diff. | −1.28 | +0.61 | +0.12 | −1.31 | −1.71 | −0.45 |
| | | Relative difference | −12 | +8 | +1 | −11 | −15 | −5 |
| PHPA | Whole Mud | Act. | 1.49 | 1.69 | 1.89 | 2.46 | 1.79 | 1.98 |
| | (g/l) | Meas. | 1.74 | 1.54 | 1.77 | 1.93 | 2.00 | 1.57 |
| | | Diff. | +0.25 | −0.15 | −0.12 | −0.53 | +0.21 | −0.41 |
| | | Relative difference | +17 | −9 | −6 | −22 | +12 | −21 |
| XC | Whole Mud | Act. | 3.02 | 1.18 | 2.20 | 2.79 | 2.41 | 2.58 |
| | (g/l) | Meas. | 1.94 | 1.51 | 1.89 | 2.30 | 2.20 | 1.57 |
| | | Diff. | −1.08 | +0.33 | −0.31 | −0.49 | −0.21 | −0.01 |
| | | Relative difference | −35 | +28 | −14 | −18 | −9 | −39 |

*Difference is [Actual − Measured]
† Relative difference is ([Actual − Meas]/Actual).100%

TABLE 4

Results for 6 test muds calculated using calibration model constructed using raw undiluted mud solids.

| | | | TEST MUD BATCH NO. | | | | | |
|---|---|---|---|---|---|---|---|---|
| | | | 1 | 2 | 3 | 4 | 5 | 6 |
| SOLIDS | | Actual | 33.20 | 29.29 | 31.29 | 32.94 | 32.74 | 30.52 |
| CONTENT | | Measured | 32.21 | 29.61 | 30.99 | 32.46 | 32.25 | 30.30 |
| (Wt. %) | | *Difference | −0.99 | +0.32 | −0.30 | −0.48 | −0.49 | −0.22 |
| | | †Relative difference | −3 | +1 | +1 | −1 | −1 | −1 |
| QUANTIFICATION OF COMPONENTS | | | | | | | | |
| OCMA | Whole Mud | Act. | 137.74 | 97.45 | 112.56 | 141.74 | 139.31 | 100.42 |
| | (g/l) | Meas. | 128.27 | 97.77 | 116.96 | 133.16 | 129.48 | 102.55 |
| | | Diff. | −9.47 | +0.32 | +4.4 | −8.58 | −9.83 | +1.02 |
| | | Relative difference | −7 | 0 | +4 | −6 | −7 | +1 |
| Soltex | Whole Mud | Act. | 9.34 | 6.35 | 10.76 | 6.37 | 6.81 | 9.32 |
| | (g/l) | Meas. | 8.89 | 8.10 | 9.72 | 7.23 | 7.10 | 8.95 |
| | | Diff. | −0.45 | +1.75 | −1.04 | +0.86 | +0.20 | −0.37 |
| | | Relative difference | −5 | +28 | −10 | +14 | +3 | −4 |
| Starch | Whole Mud | Act. | 10.00 | 7.92 | 9.14 | 11.50 | 11.13 | 9.36 |
| | (g/l) | Meas. | 10.04 | 6.63 | 8.14 | 11.75 | 10.15 | 9.62 |
| | | Diff. | +0.04 | −1.29 | −1 | +0.25 | +0.98 | +0.26 |
| | | Relative difference | 0 | −16 | 11 | +2 | −9 | +3 |
| PHPA | Whole Mud | Act. | 1.49 | 1.69 | 1.89 | 2.46 | 1.79 | 1.98 |
| | (g/l) | Meas. | 1.57 | 1.29 | 2.08 | 2.83 | 2.04 | 1.72 |
| | | Diff. | +0.08 | −0.4 | −0.19 | +0.37 | +0.25 | −0.26 |
| | | Relative difference | +5 | −24 | +10 | +15 | +14 | −13 |
| XC | Whole Mud | Act. | 3.02 | 1.18 | 2.20 | 2.79 | 2.41 | 2.58 |
| | (g/l) | Meas. | 2.52 | 1.00 | 2.43 | 2.30 | 2.24 | 2.43 |
| | | Diff. | −0.05 | −0.18 | +0.23 | −0.49 | −0.17 | −0.15 |
| | | Relative difference | −17 | −15 | +10 | −17 | −7 | −6 |

*Difference is [Actual − Measured]
† Relative difference is ([Actual − Meas]/Actual).100%

TABLE 5

Results for 6 test muds calculated using calibration model constructed using mud solids diluted in potassium bromide.

| | | TEST MUD BATCH NO. | | | | | |
|---|---|---|---|---|---|---|---|
| | | 1 | 2 | 3 | 4 | 5 | 6 |
| SOLIDS | Actual | 22.14 | 23.40 | 23.97 | 22.34 | 23.16 | 25.18 |
| CONTENT | Measured | 22.13 | 23.56 | 24.08 | 22.57 | 23.37 | 25.59 |
| (Wt. %) | *Difference | −0.01 | +0.16 | +0.11 | +0.23 | +0.21 | +0.41 |
| | †Relative difference | 0 | +1 | 0 | +1 | +1 | −2 |

TABLE 5-continued

Results for 6 test muds calculated using calibration model constructed using mud solids diluted in potassium bromide.

| | | | TEST MUD BATCH NO. | | | | | |
|---|---|---|---|---|---|---|---|---|
| | | | 1 | 2 | 3 | 4 | 5 | 6 |
| QUANTIFICATION OF COMPONENTS | | | | | | | | |
| Bentonite | Whole Mud (g/l) | Act. | 35.86 | 25.91 | 38.02 | 44.22 | 19.96 | 48.00 |
| | | Meas. | 34.54 | 21.62 | 39.38 | 43.18 | 20.62 | 44.59 |
| | | Diff. | −1.32 | −4.29 | +1.36 | −1.04 | +0.66 | −3.41 |
| | | Relative difference | −4 | −16 | +4 | −2 | +3 | −7 |
| CMC-LV | Whole Mud (g/l) | Act. | 9.97 | 14.51 | 9.11 | 7.60 | 12.46 | 8.50 |
| | | Meas. | 9.42 | 13.91 | 7.86 | 6.58 | 14.43 | 7.36 |
| | | Diff. | −0.55 | −0.60 | −1.25 | −1.02 | +1.97 | −1.14 |
| | | Relative difference | −5 | −4 | −14 | −13 | +16 | −13 |
| XC | Whole Mud (g/l) | Act. | 1.00 | 1.58 | 3.71 | 3.46 | 3.62 | 2.60 |
| | | Meas. | 1.03 | 1.61 | 4.56 | 3.70 | 2.98 | 2.45 |
| | | Diff. | +0.03 | −0.03 | +0.85 | +0.24 | −0.64 | −0.15 |
| | | Relative difference | +3 | +2 | +23 | +7 | −18 | −6 |
| Calcite | Whole Mud (g/l) | Act. | 29.87 | 27.94 | 33.95 | 26.17 | 34.89 | 31.99 |
| | | Meas. | 30.08 | 27.55 | 34.68 | 25.85 | 36.96 | 31.78 |
| | | Diff. | +0.21 | +0.39 | +0.73 | −0.32 | +2.07 | −0.21 |
| | | Relative difference | +1 | +1 | +2 | −1 | +6 | −1 |
| Barite | Whole Mud (g/l) | Act. | 187.16 | 212.29 | 205.38 | 185.07 | 207.78 | 208.14 |
| | | Meas. | 187.98 | 218.95 | 206.25 | 187.04 | 200.89 | 210.38 |
| | | Diff. | +0.82 | +6.66 | +0.87 | +1.97 | −6.89 | +2.24 |
| | | Relative Difference | 0 | +3 | 0 | +1 | −3 | +1 |

*Difference is [Actual − Measured]
† Relative difference is ([Actual − Meas]/Actual).100%

TABLE 6

Results for 6 test muds calculated using calibration model constructed using raw undiluted mud solids.

| | | | TEST MUD BATCH NO. | | | | | |
|---|---|---|---|---|---|---|---|---|
| | | | 1 | 2 | 3 | 4 | 5 | 6 |
| SOLIDS CONTENT (Wt. %) | | Actual | 22.14 | 23.40 | 23.97 | 22.34 | 23.16 | 25.18 |
| | | Measured | 22.13 | 23.56 | 24.08 | 22.57 | 23.37 | 25.59 |
| | | *Difference | −0.01 | +0.16 | +0.11 | +0.23 | +0.21 | +0.41 |
| | | †Relative difference | 0 | +1 | 0 | +1 | +1 | −2 |
| QUANTIFICATION OF COMPONENTS | | | | | | | | |
| Bentonite | Whole Mud (g/l) | Act. | 35.86 | 25.91 | 38.02 | 44.22 | 19.96 | 48.00 |
| | | Meas. | 40.93 | 34.54 | 42.34 | 42.43 | 20.54 | 47.97 |
| | | Diff. | +5.07 | +8.63 | −4.32 | −1.79 | +0.58 | −0.03 |
| | | Relative difference | +14 | +33 | −3 | −4 | +3 | 0 |
| CMC-LV | Whole Mud (g/l) | Act. | 9.97 | 14.51 | 9.11 | 7.60 | 12.46 | 8.50 |
| | | Meas. | 7.36 | 12.93 | 11.06 | 10.15 | 11.87 | 6.73 |
| | | Diff. | −2.61 | −1.58 | +1.95 | +2.55 | −0.59 | −1.77 |
| | | Relative difference | −26 | −11 | +21 | +34 | −5 | −21 |
| XC | Whole Mud (g/l) | Act. | 1.00 | 1.58 | 3.71 | 3.46 | 3.62 | 2.60 |
| | | Meas. | 1.50 | 1.67 | 4.21 | 3.38 | 2.93 | 3.44 |
| | | Diff. | +0.5 | +0.09 | +0.5 | −0.08 | −0.69 | +0.84 |
| | | Relative difference | +50 | +6 | +13 | −2 | −20 | +32 |
| Calcite | Whole Mud (g/l) | Act. | 29.87 | 27.94 | 33.95 | 26.17 | 34.89 | 31.99 |
| | | Meas. | 25.89 | 30.00 | 34.24 | 27.00 | 34.53 | 30.52 |
| | | Diff. | −3.98 | +2.06 | +0.29 | +0.83 | −0.36 | −1.38 |
| | | Relative difference | −13 | +7 | +1 | +3 | −1 | −4 |
| Barite | Whole Mud (g/l) | Act. | 187.16 | 212.29 | 205.38 | 185.07 | 207.78 | 208.14 |
| | | Meas. | 180.77 | 209.44 | 202.62 | 182.59 | 202.84 | 211.88 |
| | | Diff. | −6.39 | −2.85 | −2.76 | −2.48 | −4.94 | +3.74 |
| | | Relative difference | −3 | −1 | −1 | −1 | −2 | +2 |

*Difference is [Actual − Measured]
† Relative difference is ([Actual − meas]/Actual).100%

We claim:

1. Method of quantitative analysis of products in a drilling fluid, said method comprising the steps of:
   obtaining a sample of said drilling fluid,
   determining a sample density,
   drying a know weight of said sample to constant weight so as to obtain products in the form of dried solids,
   determining a weight fraction of solids in said sample,
   preparing a known weight of dried solids to form a powder suitable for infrared analysis,
   analysing the powered in a spectrometer to obtain an infrared spectrum including contributions from at least one organic product and at least one inorganic product, and
   determining a value characteristic of the concentration of said at least one organic product and said at least one inorganic product in the drilling fluid from said spectrum, said determined sample density and said determined weight fraction of solids in said sample.

2. The method of claim 1, further comprising the step of interpreting the infrared spectrum to determine the weight percent of said at least one organic product and at least one inorganic product in the powder.

3. The method of claim 1 wherein the infrared spectrum is obtained by a diffuse reflectance technique.

4. The method of claim 3, wherein a transmission spectrum equivalent to the spectrum obtained by the diffuse reflectance technique is obtained by performing a Kubelka-Munk transform on said spectrum.

5. The method of claim 1, further comprising the steps of determining a weight of salt dissolved in a known weight of drilling fluid and correcting the weight fraction of solids in the drilling fluid to account for said weight of salt.

6. The method of claim 1, wherein the drilling fluid sample is dried to constant weight using an infrared drier balance.

7. The method of claim 1, wherein the step of preparing a known weight of dried solids to form a powder suitable for infrared analysis is performed without addition of any additives thereto or carries therefore.

8. The method of claim 1, wherein the step of preparing a known weight of dried solids to form a powder comprises mixing a known weight of dried solids with a halide salt to form a mixture and grinding the mixture until the solids have a particle size of no more than 10 microns to obtain said powder.

9. The method in accordance with claim 8 wherein the halide salt is potassium bromide or sodium chloride.

10. The method of claim 1, wherein the step of determining a value characteristic of the concentration of at least one organic product and at least one inorganic product from the infrared spectrum comprises obtaining infrared spectra of standards containing known concentrations of products in said drilling fluid and generating a calibration model from said infrared spectra.

11. The method of claim 1, wherein the infrared spectrum obtained by analysing the powder is a Fourier transform infrared spectrum.

12. The method of claim 1, wherein said at least one inorganic product is selected from the group consisting of drilled clay, bentonite clay, barite, carbonates and quartz and said at least one organic product is a polymer.

13. The method of claim 1, in which a given concentration of the products is indicated in a drilling fluid specification, further comprising the steps of comparing the indicated concentration with a determined concentration of said products and adjusting the concentration of said products so as to comply with the drilling fluid specifications.

14. The method of claim 1, further comprising the step of assessing a working condition of mud solids equipment by monitoring any variation in quantity of a product treated by the mud solids equipment.

15. The method of claim 14, wherein the working condition of the mud solids equipment is assessed by comparing the quantity of one of the products treated by the mud solids equipment, upstream and downstream of said mud solids equipment.

16. The method of claim 1 further comprising the step of controlling a drilling operation by monitoring the concentration of products present in the drilling fluid and coming from the borehole wall.

17. Method of quantitative analysis of products in a drilling fluid, said method comprising the steps of:
  obtaining a sample of said drilling fluid,
  determining a sample density,
  drying a known weight of said sample to constant weight so as to obtain products in the form of dried solids,
  determining a weight fraction of solids in said sample,
  preparing a known weight of dried solids to form a powder suitable for infrared analysis,
  analysing the powder in a spectrometer to obtain an infrared spectrum including contributions from at lest one organic products and at least one inorganic product, and
  determining a value characteristic of the concentration of at least one polymer and at least one inorganic product in the drilling fluid from said spectrum, said determined sample density and said determined weight fraction of solids in said sample.

* * * * *